United States Patent [19]
Kikumoto

[11] Patent Number: 5,350,520
[45] Date of Patent: Sep. 27, 1994

[54] METHOD FOR COLLECTING THE COMPONENTS OF A SAMPLE SEPARATED BY CHROMATOGRAPHY

[75] Inventor: Mamoru Kikumoto, Ukyo, Japan
[73] Assignee: Shimadzu Corporation, Kyoto, Japan
[21] Appl. No.: 144,607
[22] Filed: Nov. 1, 1993

Related U.S. Application Data

[63] Continuation of Ser. No. 867,400, Apr. 13, 1992, abandoned.

[30] Foreign Application Priority Data

Apr. 25, 1991 [JP] Japan .................... 3-124683

[51] Int. Cl.⁵ .............................................. B01D 15/08
[52] U.S. Cl. ................................... 210/656; 210/198.2
[58] Field of Search ............... 210/635, 656, 659, 101, 210/198.2; 73/61.52, 61.57, 61.58; 436/161; 422/70

[56] References Cited

U.S. PATENT DOCUMENTS

| | | | |
|---|---|---|---|
| 3,686,117 | 8/1972 | Lauer | 210/198.2 |
| 3,717,028 | 2/1973 | Annino | 73/23.1 |
| 4,204,952 | 5/1980 | Snyder | 210/659 |
| 4,274,967 | 6/1981 | Snyder | 210/659 |
| 4,455,084 | 6/1984 | Webb | 210/659 |
| 4,478,713 | 10/1984 | Girot | 210/101 |
| 4,579,663 | 4/1986 | Poile | 210/656 |
| 4,719,017 | 1/1988 | Uchino | 210/656 |
| 4,724,081 | 2/1988 | Kawahara | 210/659 |
| 4,762,617 | 8/1988 | Stevens | 210/656 |
| 4,802,981 | 2/1989 | Kenney | 210/656 |
| 4,806,250 | 2/1989 | Takata | 210/659 |
| 4,861,488 | 8/1989 | Kenney | 210/656 |
| 4,885,143 | 12/1989 | Schmuckler | 210/656 |
| 5,100,557 | 3/1992 | Nogami | 210/656 |
| 5,121,443 | 6/1992 | Tomlinson | 210/656 |

FOREIGN PATENT DOCUMENTS 406757 1/1991 European Pat. Off. ........... 210/656

*Primary Examiner*—Ernest G. Therkorn
*Attorney, Agent, or Firm*—Wegner, Cantor, Mueller & Player

[57] ABSTRACT

Method and apparatus for separately collecting the components of a sample separated by chromatography, which uses a time schedule starting from a specific peak on the chromatogram of a sample to be analyzed and comprising those time bands of a first group in each of which peaks are to be detected and those time bands of a second group in each of which peaks are to be neglected, the time bands of the first and second groups occurring alternately and successively, and only in the time bands of the first group collection of a sample component is conducted while a peak is being detected.

6 Claims, 2 Drawing Sheets

METHOD FOR COLLECTING THE COMPONENTS OF A SAMPLE SEPARATED BY CHROMATOGRAPHY

This application is a continuation of U.S. application Ser. No. 07/867,400 filed Apr. 13, 1992, now abandoned.

BACKGROUND OF THE INVENTION

This invention relates to a method and apparatus for separately collecting the components of a sample separated by chromatography.

In a known method of collecting separated sample components by using a liquid chromatograph, the operation is controlled in accordance with a time schedule preset on the basis of the time: of sample injection and the retention times of the components of a sample in such a manner that collection is conducted for a period of time in which a sample component of interest is supposed to continuously elute from the chromatograph. Since the retention time of a sample varies with temperature, the kind of the mobile phase used, or the amount of the sample injected, a time lag is likely to occur between the collecting operation and the period of time during which the sample component to be collected elutes from the column of the chromatograph.

To enable accurate collection there have been proposed various methods, in one of which not only the time schedule indicating the periods of time during which the respective sample components are supposed to elute is relied upon, but also the rising edge of a peak on the chromatogram indicative of a sample component actually eluting is detected, or whether or not the output of the detector of the chromatograph exceeds a predetermined level is checked, so that collection of the sample component of interest is conducted upon confirmation of the actual elution of the sample component from the chromatographic column.

In another of the known methods, the retention time of a sample component from the time of injection of the sample as a starting point is not relied upon, but a specific peak, say, the first peak on the chromatogram is used as a starting point for the time schedule thereby to reduce the time lag between the retention time of a sample component of interest and the time of the collecting operation.

The above-mentioned prior art method, which uses not only the retention time of a sample component with the injection time of the sample as a starting point but also confirmation of the existence of the rising edge of a peak on the chromatogram or the level of the output of the detector of the chromatograph to conduct the operation of collecting the sample component of interest, is not useful when the retention time of a sample component to be collected differs so greatly from that preset in the time schedule that no peak is detected during the period of time in which a peak is expected to appear.

The prior art method, which uses a time schedule which starts at a specific peak on the chromatogram, is not adversely influenced by a lag in the retention time. Since collection is conducted only during a predetermined period of time upon lapse of a predetermined period of time after a specific peak on the chromatogram, the method cannot deal with variation of the amount of a sample component. If the amount of a sample component to be collected is large, the rising and descending end portions of the peak may not be collected. On the contrary, if the amount is small, a large amount of the mobile phase is collected thereby to reduce the concentration of the collected sample component.

SUMMARY OF THE INVENTION

Accordingly, the primary object of the invention is to provide a method and an apparatus for collecting the separated components of a sample effluent from a liquid chromatograph, which can eliminate the above-mentioned disadvantages of the conventional devices.

The present invention uses a time schedule which is set with a specific peak on the chromatogram taken as a starting point and comprises those time bands of a first group in each of which peaks are to be detected and those time bands of a second group in each of which peaks are to be neglected, the time bands of the first and second groups occurring alternately and successively, and only in the time bands of the first group collection of a sample component is conducted while a peak is being detected.

The conventional method, in which collection of a sample component is conducted in accordance with a time schedule which is started at a specific peak, is less influenced than otherwise by a great change in the retention time of a sample component. In the present invention, since the time schedule is set with a specific peak as a starting point and comprises those time bands in which collection of a sample component is conducted and those time bands in which collection of a sample component is not conducted, a similar advantage is obtained. With this arrangement alone, however, if the amount of a sample component is large, the whole eluted sample component cannot be collected, and if the eluted amount is small, the concentration of the collected sample component is reduced due to the mobile phase unintentionally collected at the same time.

In accordance with the present invention, the time schedule is intended not to determine directly the time at which the collecting operation is to be started or stopped, but to set those time bands during which peak detection is conducted. This completely eliminates any adverse influence on the collecting operation when the peak position has been more or less shifted or when the peak height has changed.

DESCRIPTION OF THE DRAWINGS

The invention will be described in more detail with reference to the accompany drawings, wherein.

PREFERRED EMBODIMENTS OF THE INVENTION

Figure 1:
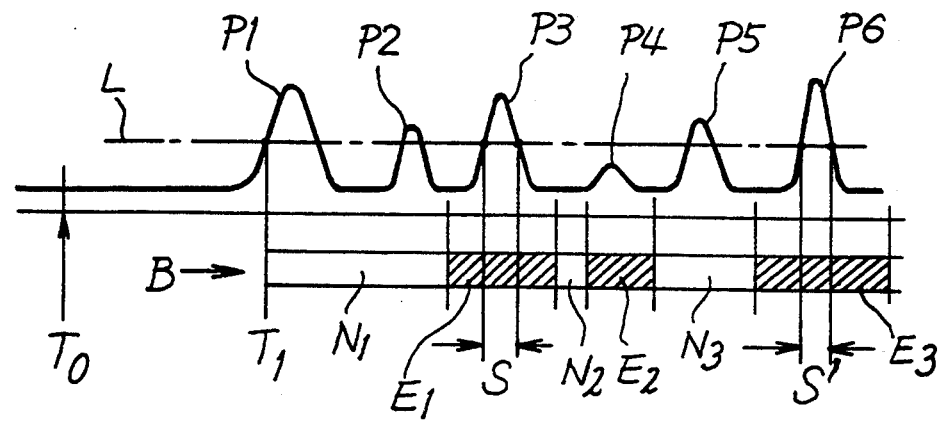
FIG. 1 schematically shows the principle of the operation of the invention.

The operation of one embodiment of the invention will be described with reference to FIG. 1, which shows a chromatogram drawn in real time as a chromatograph is operated. In FIG. 1, the reference symbol $T_0$ designates the time at which a sample is injected into the column of the chromatograph, and the reference symbol $P_1$ designates a specific peak which is the first peak on the chromatogram in this embodiment. The reference symbol L designates a level for determining the existence of a peak. In particular, if the output from the detector of the chromatograph exceeds, and remains above, the level, it is decided that a peak exists. At the rising side of the peak $P_1$, the output from the detector exceeds the level L at time $T_1$, whereupon a time schedule B starts, which comprises a first group of time bands E shown hatched and a second group of time bands N shown blank. The time bands E and N are arranged alternately. Peaks are detected in each of the time bands E while peaks are neglected in each of the time bands N. A second peak $P_2$ appears in the time band $N_1$ in which peaks are to be neglected, so that nothing is done. A third peak $P_3$ appears in the time band $E_1$ in which peaks are to be detected, so that it is checked whether or not the output from the detector exceeds the level L. During the period of time S in which the output remains above the level L, the effluent from the column of the chromatograph is collected. A fourth peak $P_4$ appears in the time band $E_2$ in which peaks are to be detected. Since the peak $P_4$ does not exceed the level L, however, it is decided that no peak exists in the time band $E_2$, so that no collecting operation is conducted. The next peak $P_5$ appears in the time band $N_3$ in which peaks are to be neglected, so that no collecting operation is conducted. As the next peak $P_6$ appears in the time band $E_3$, a collecting operation is conducted for a period of time $S'$ as with the peak $P_3$.

In the above embodiment, whether peaks are to be detected or neglected depends upon whether or not the output from the detector exceeds a predetermined level. Any known method may be used for peak detection. For example, a chromatogram may be differentiated, and the points at which the differentiated value exceeds a predetermined positive level and a predetermined negative level may be considered as a start and an end point of a peak, respectively.

Figure 2:
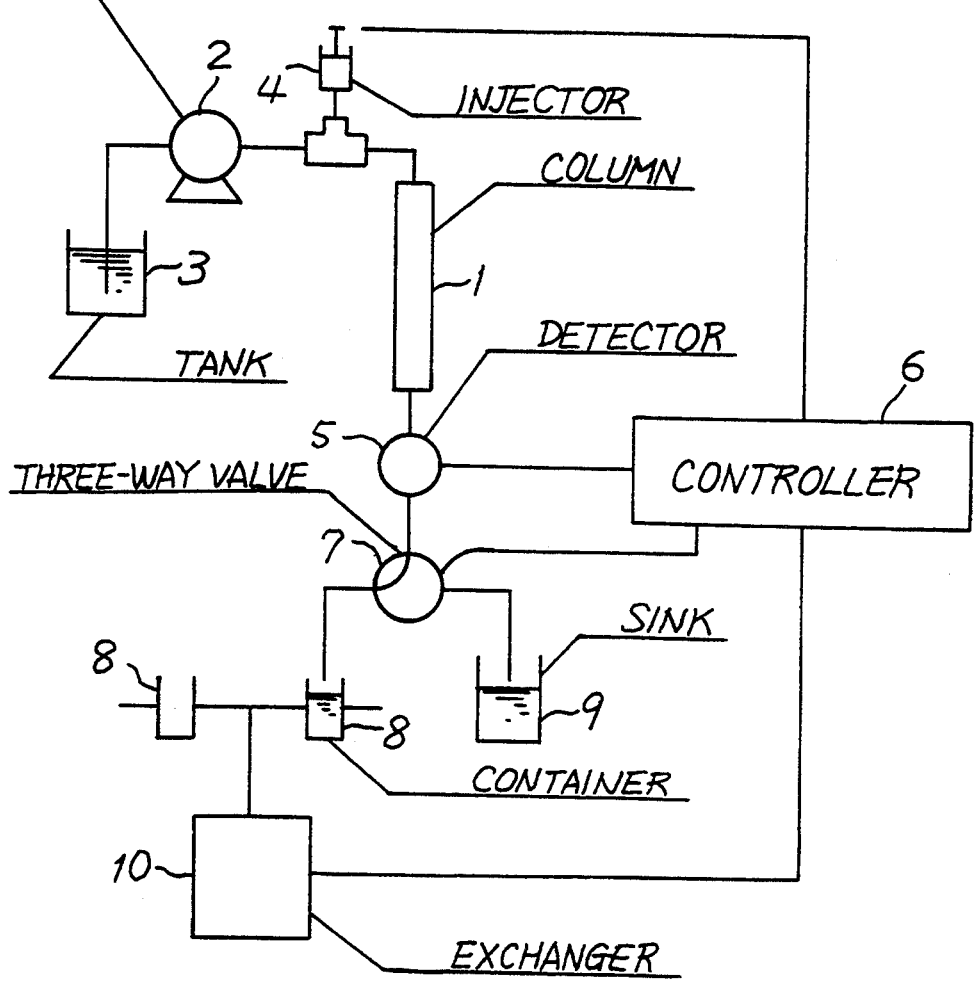
FIG. 2 is a block diagram of one embodiment of the invention.

FIG. 2 shows a schematic layout of the apparatus in accordance with one embodiment of the invention. A pump 2 supplies mobile phase from a tank 3 into a chromatographic column 1. A sample is introduced into the chromatograph at the inlet side of the column 1 by means of an injector 4.

A detector 5 is provided at the outlet side of the column 1. The output of the detector 5 is applied to a controller B, which controls a three-way valve 7 so as to direct the eluate from the column 1 to one of a plurality of containers 8 and alternatively to a sink 9. When different sample components are to be collected separately, an exchanger 10 is operated by the controller 6 to exchange the container filled with a component for a different, empty one of the containers.

Figure 3:
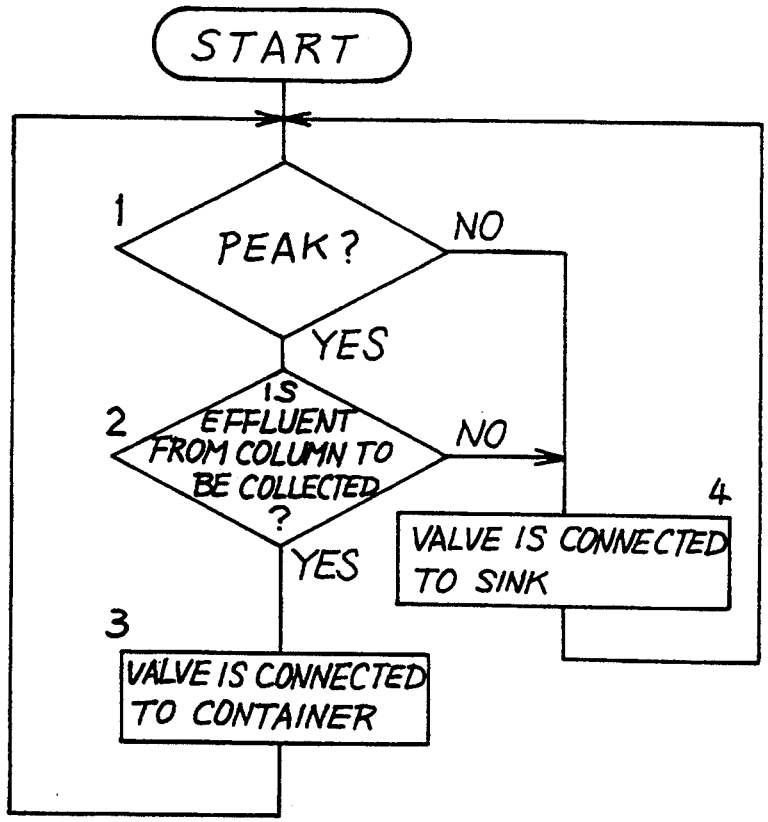
FIG. 3 is a flow chart of the operation of the controller in the embodiment of FIG. 2.

FIG. 3 shows a flow chart of the operation of the controller 6. A time schedule prepared for proper operation of the apparatus is set beforehand in the controller 8. For example, the time schedule starts at the time a specific peak is detected and comprises a series of time bands (2.8–2.6–3.0–2.6–3.0–4.0 . . . ).

This means that peaks are to be detected for a period of 2.8 minutes from the starting point, that peaks are to be neglected for a succeeding period of 2.6 minutes, that peaks are to be detected for a succeeding period of 3.0 minutes, and so on, so that those time bands in which peaks are to be detected alternate with those time bands in which peaks are to be neglected.

Upon injection of a sample into the chromatograph the controller 8 starts its operation in accordance with the above-mentioned time schedule. When a first peak, that is, the specific peak in the present embodiment is detected, the first time band of the time schedule is entered and the component of the sample causing the peak is collected, with the valve 7 connecting the column 1 to a predetermined one of the containers 8. When a second peak appears (step 1), it is checked if the second peak is in the time band in which peaks are to be detected, that is, the effluent from the column 1 is to be collected, or if it is in the time band in which peaks are to be neglected, that is, the effluent from the column is to be discarded (step 2). If the peak is in the time band in which peaks are to be detected, the three-way valve 7 is operated to connect the column to the next one of the containers 8, into which the effluent from the column 1 corresponding to the second peak is collected (step 3). When the collection has been completed, the operation is returned to step 1, with the valve 7 having been switched over to the sink 9.

Even when a peak appears, if it is in the time band in which peaks are to be neglected (step 2), the valve 7 is kept connected to the sink 9, and the operation is returned to step 1.

In the above embodiment, the specific peak is the first peak. The specific peak need not necessarily be the first peak on the chromatogram. Nor need it be collected. A particularly marked peak on a chromatogram may be selected as a specific peak. A material having an appropriate retention time may be added to a sample to be analyzed, so that the peak caused by the added material may be selected as a specific peak. For detection the specific peak may be identified as such by the order of the peak on the chromatogram. Since such a specific peak has a particularly marked height, a specific level higher than the level for detection of the sample components to be collected may be set for discrimination of the specific peak so that the time schedule may start from the time when the output from the detector exceeds the specific level and the effluent from the column may not be collected during the first time band in the time schedule.

Figure 4:
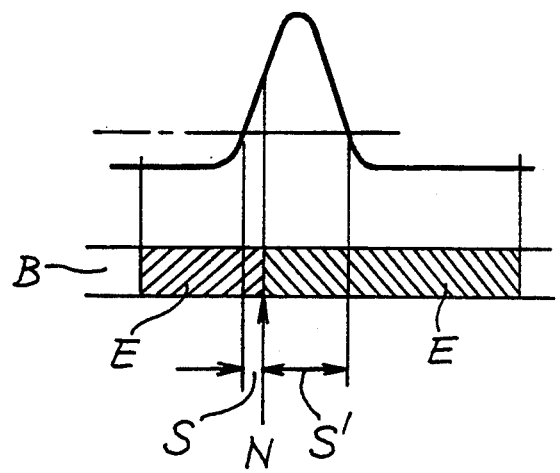
FIG. 4 schematically shows a particular operation of the apparatus of the invention.

As shown in FIG. 4, a time band N, in which peaks are to be neglected and which is situated between two of the time bands E in which peaks are to be detected, may be set to zero minutes so as to define a so-called "zero-width" time band N and to provide, in effect, that the two time bands E are adjacent, and in order that the valve 7 may be operated to change connection of the column 1 from one to another of the containers 9. With this arrangement, it is possible to collect the initial portion of a single peak or sample component which has a lower purity and the remaining main portion thereof which has a higher purity into separate containers.

In accordance with the invention, even when the retention times or peak heights of the components of a sample being separated by a liquid chromatograph change greatly, it is possible to collect the sample components accurately without making erroneous collection, loss of the collected components or reduction of their concentrations.

What is claimed is:

1. A method of collecting components of a sample separated by chromatography, comprising:
setting a time schedule which starts from a specific peak on a chromatogram of a sample whose components are to be separately collected;
providing said time schedule with a series of time bands of a first group, in each of which peaks on said chromatogram are to be detected for possible utilization in controlling collecting of said sample components, and a series of time bands of a second group, in each of which peaks on said chromatogram are to be neglected, said time bands of said first and second groups occurring alternately and successively;

using a units of time setting in selecting a time length of each of said time bands, individually;

introducing said sample into a chromatograph;

detecting said specific peak to start said time schedule;

detecting at least one peak on the chromatogram of said sample in at least one of said time bands of said first group;

disregarding any peaks on the chromatogram of said sample occurring in said time bands of said second group; and collecting a component of said sample that is causing said at least one peak.

2. The method of claim 1, wherein said specific peak is the first peak on said chromatogram.

3. The method of claim 1, wherein said specific peak is a peak at a predetermined position on said chromatogram.

4. The method as in claim 1, and further comprising the steps of:

adding a material having a predetermined retention time to said sample prior to said collecting in order to provide said specific peak.

5. The method as in claim 4, and further comprising the steps of:

setting a detection level for said peaks of said sample components;

providing that said specific peak has a predetermined height greater than peaks which are caused by the components of said sample and;

setting a specific detection level, higher than said detection level for said peaks of said sample components, for said specific peak so that a peak has exceeded said specific level may be identified as said specific peak.

6. The method of claim 1, and further comprising the steps of:

providing at least one particular time band of said second group, between and adjacent two of said time bands of said first group;

entering zero for said units of time of said particular time band, so that a particular peak resulting from a single sample component can extend over said particular time band of said second group and in said two time bands of said first group; and collecting each of two separate portions of the single sample component causing said particular peak in corresponding separate ones of said two time bands of said first group.

* * * * *